United States Patent
Toumazou et al.

(10) Patent No.: US 7,649,358 B2
(45) Date of Patent: Jan. 19, 2010

(54) SIGNAL PROCESSING CIRCUIT COMPRISING ION SENSITIVE FIELD EFFECT TRANSISTOR AND METHOD OF MONITORING A PROPERTY OF A FLUID

(75) Inventors: Christofer Toumazou, Oxford (GB); Bhusana Premanode, London (GB); Leila Shepherd, Weybridge (GB)

(73) Assignee: DNA Electronics Ltd., London (GB)

( * ) Notice: Subject to any disclaimer, the term of this patent is extended or adjusted under 35 U.S.C. 154(b) by 377 days.

(21) Appl. No.: 11/572,050

(22) PCT Filed: Jun. 22, 2005

(86) PCT No.: PCT/GB2005/050095

§ 371 (c)(1),
(2), (4) Date: Jan. 12, 2007

(87) PCT Pub. No.: WO2006/005967

PCT Pub. Date: Jan. 19, 2006

(65) Prior Publication Data
US 2008/0265985 A1     Oct. 30, 2008

(30) Foreign Application Priority Data
Jul. 13, 2004   (GB) ................................ 0415633.7

(51) Int. Cl.
*G01N 27/414*  (2006.01)
*G01N 27/26*   (2006.01)
*G01F 1/64*    (2006.01)

(52) U.S. Cl. ................... 324/438; 205/789; 257/253; 204/433

(58) Field of Classification Search ................ 324/438; 205/789; 257/253; 204/433
See application file for complete search history.

(56) References Cited

U.S. PATENT DOCUMENTS 4,793,825 A   12/1988  Benjamin et al.

(Continued)

FOREIGN PATENT DOCUMENTS

GB          2389424       12/2003

(Continued)

OTHER PUBLICATIONS

Bergveld, P., "ISFET, Theory and Practice," IEEE Sensor Conference, Toronto, Oct. 2003.

(Continued)

*Primary Examiner*—Timothy J Dole
*Assistant Examiner*—John Zhu
(74) *Attorney, Agent, or Firm*—Nixon & Vanderhye, P.C.

(57) ABSTRACT

A signal processing circuit includes an ion sensitive field effect transistor, a reference electrode for the ion sensitive field effect transistor, a metal oxide semiconductor transistor having its gate coupled to the reference electrode, and a biasing circuit. The biasing circuit is configured to bias the ion sensitive field effect transistor and the metal oxide semiconductor field effect transistor to operate in a weak inversion region and to provide an output current signal.

8 Claims, 7 Drawing Sheets

U.S. PATENT DOCUMENTS

| | | | |
|---|---|---|---|
| 5,250,168 A * | 10/1993 | Tsukada et al. | 204/416 |
| 5,309,085 A * | 5/1994 | Sohn | 257/253 |
| 5,334,888 A * | 8/1994 | Bodas | 326/54 |
| 5,583,462 A * | 12/1996 | Grasshoff | 327/262 |
| 5,911,873 A * | 6/1999 | McCarron et al. | 205/789 |
| 6,657,269 B2 * | 12/2003 | Migliorato et al. | 257/414 |
| 6,856,161 B2 * | 2/2005 | Thewes | 324/769 |
| 2004/0134798 A1 * | 7/2004 | Toumazou et al. | 205/793.5 |

FOREIGN PATENT DOCUMENTS

| | | |
|---|---|---|
| JP | 2000055874 A * | 2/2000 |
| WO | 03/073088 | 9/2003 |
| WO | 2004/040291 | 5/2004 |

OTHER PUBLICATIONS

Martinoia, S. et al,. "A behavioral macromodel of the ISFET in Spice," Sensors and Actuators B, Elsevier Sequoia A.A., Lausanne, CH, vol. 62, No. 3, pp. 182-189, Mar. 2000, XP004194214.

Purushothaman, S. et al, "Towards Fast Solid State DNA Sequencing," Proc IEEE Int., vol. 4, pp. IV/169-IV/172, (2002).

Shepherd, L. et al., "Weak Inversion ISFETs for ultra-low power biochemical sensing and real-time analysis," Sensors and Actuators B, Elsevier Sequoia S.A., Lausanne, Ch, vol. 107, No. 1, pp. 468-473, May 27, 2005, XP004900008.

* cited by examiner

| pH | Vinth (mV) |
|---|---|
| 1 | -63.5 |
| 2 | -37.6 |
| 3 | -11.63 |
| 4 | 14.24 |
| 5 | 40.0 |
| 6 | 65.8 |
| 7 | 91.7 |
| 8 | 117.7 |
| 9 | 143.7 |
| 10 | 169.7 |
| 11 | 195.7 |
| 12 | 221.7 |
| 13 | 247.6 |
| 14 | 273.6 |

SIGNAL PROCESSING CIRCUIT COMPRISING ION SENSITIVE FIELD EFFECT TRANSISTOR AND METHOD OF MONITORING A PROPERTY OF A FLUID

FIELD OF THE INVENTION

The present invention relates to ion sensitive field effect transistors and to processing and control systems utilising ion sensitive field effect transistors.

BACKGROUND

Figure 1:
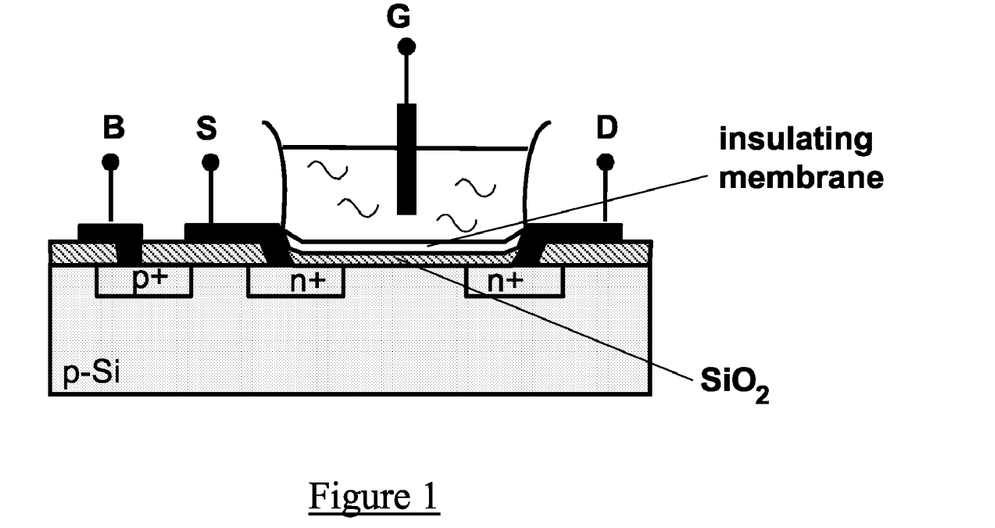
FIG. 1 illustrates schematically an ISFET in a typical use scenario.
Figure 2:
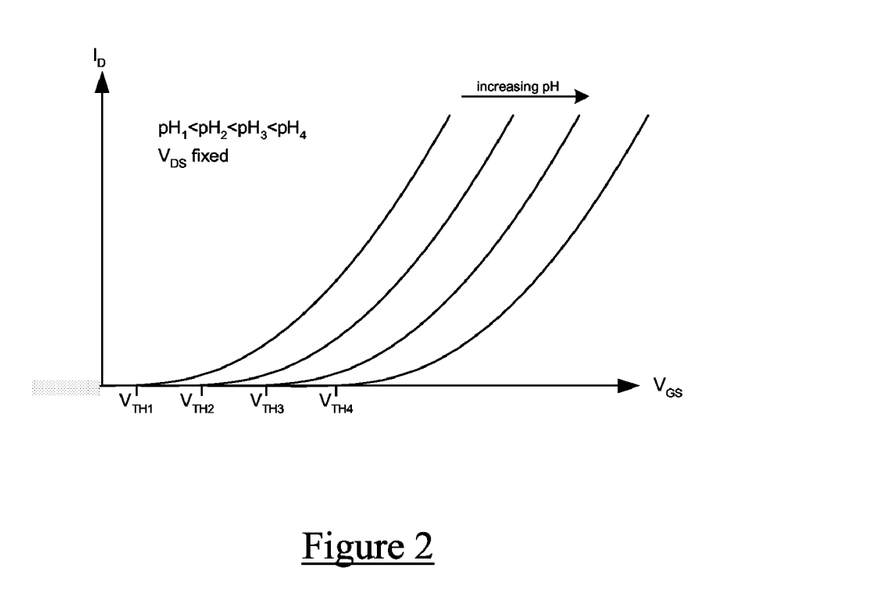
FIG. 2 shows the $I_D$-$V_{GS}$ characteristics of the ISFET of FIG. 1 at various pH levels.

The ion-sensitive field effect transistor (ISFET) is based on a MOSFET with a remote gate (or "reference electrode") lying beneath a chemically-sensitive insulator. The surface of the insulator is exposed to an electrolyte upon which measurements are to be made. A typical ISFET use scenario is illustrated in FIG. 1. Field effects from ionic charge interaction at the insulator surface cause shifts in the ISFET drain current vs gate to source voltage ($I_D$-$V_{GS}$) characteristic as illustrated in FIG. 2. The insulator in contact with the electrolyte is chosen according to its chemical properties and sensitivity to a particular ion.

For ISFETs designed to measure the pH of an electrolyte, i.e. the H+ ion content of the electrolyte, silicon nitride and aluminium oxide membranes are commonly used to insulate the gate. ISFETs can be made sensitive to ions other than H$^+$ through the choice of the ion-sensitive membrane, thus adding an element of ion-selectivity. ISFETs whose membrane is modified to be selective to a particular ionic species are known as ChemFETs, with a further variation, known as EnFETs, using enzymes in close proximity to the membrane surface. It has also been shown that even conventional pH-ISFETs with unmodified $Si_3N_4$ membranes exhibit a limited but measurable sensitivity to K$^+$ and Na$^+$ ions. This said, practical and commercial applications of the ISFET for applications other than pH sensing are rare. Nonetheless, in the following discussion, the term ISFET is used both specifically to refer to a pH sensor and generally to refer to all ion and enzyme sensitive FETs operating on similar principles.

The attractiveness of ISFETs and their FET-based counterparts is that they are compatible with the standard fabrication processes used to mass produce computer chips and can therefore be reliably and cost-effectively produced. Importantly, processing circuitry can be integrated onto the same chip as the ISFET device itself. The integration of intelligent circuitry with the sensing device itself is what is required for the development of so-called "smart sensors" which require robustness to non-ideal sensing conditions, as well as to provide electronics to discriminate between chemicals "on-chip".

The normal operating mode of an ISFET is the strong inversion region of the $I_D$-$V_{GS}$ characteristic. In this region, the gate to source voltage exceeds the threshold voltage $V_{TH}$, resulting in a strong inversion of the channel underlying the gate. For this mode of operation, drain current is related to the gate voltage by a square law or linear relationship.

Referring again to FIG. 1, any voltage applied to the reference electrode of an ISFET is capacitively-coupled via the electrolyte to the insulator surface, where a pH-dependent charge from ions on this interface modulates the channel current, causing the observed shifts in the ISFET transfer characteristic, thereby modulating its threshold voltage $V_{th}$. Assuming that the ISFET is operated in the constant drain current mode, with a constant drain-source voltage, the gate to source voltage directly reflects the pH-sensitive interfacial potential at the gate interface, that is:

$$pH = pH_{cal} + V_{gs}/S, \quad (1)$$

where $pH_{cal}$ is the pH of a calibration liquid at 37° C. and S is the pH sensitivity of the ISFET. The derivation of this relationship is detailed further in "ISFET, Theory and Practice", P. Bergveld, IEEE Sensor Conference, Toronto, October 2003. However, this approach assumes a constant temperature, and in any practical approach temperature compensation must be applied.

The conventional approach to compensating measurements for temperature effects is to model the temperature dependence of a system, measure the temperature in parallel with the pH, and correct the measured pH on the basis of the model and the measured temperature. Whilst effective, this approach has a number of disadvantages. Firstly, it relies upon the provision of a temperature sensor, typically comprising a temperature sensitive resistor integrated onto the same chip as the ISFET. Secondly, processing power must be provided to perform the correction. Thirdly, the process of correcting the measured pH values takes time. In a typical system, pH and temperature values are converted into their digital equivalents, prior to carrying the further processing with a microprocessor or CPU. If necessary, digital control outputs are converted into analogue equivalents prior to application to a device to be controlled.

It has long been recognised that a key area in which ISFETs can be applied is that of implantable and wearable sensors. The requirements of conventional ISFET design outlined in the previous paragraph do not sit well with such sensors which require to be small, to consume low levels of power, and to be extremely accurate. Especially where the sensors form part of a control loop, e.g. controlling a drug delivery system, they must also be extremely accurate.

BRIEF SUMMARY

According to a first aspect of the technology disclosed herein there is provided a signal processing circuit comprising one or more ion sensitive field effect transistors and a biasing circuit for biasing the or each ion sensitive field effect transistor to operate in the weak inversion region.

Embodiments of the technology disclosed herein have the significant advantage that an output of the or each ion sensitive field effect transistor is compensated for the effects of temperature on the sensed ion by the intrinsic characteristics of the ion sensitive field effect transistor.

Preferably, the signal processing circuit comprises means for generating a current proportional to the gate voltage of the ion sensitive field effect transistor.

Preferably the or each ion sensitive field effect transistor and the biasing circuit are integrated onto a single chip.

The signal processing circuit may be configured to determine, in use, the hydrogen ion concentration of a medium to which the ion sensitive field effect transistor(s) is (are) exposed.

Preferably, the signal processing circuit comprises one or more MOSFET devices coupled to the or each ISFET, and a biasing circuit for biasing the or each MOSFET to operate in the weak inversion mode. More preferably, the ISFET(s), MOSFET(s), and biasing circuits are integrated onto a single chip.

The signal processing circuit may comprise one or more bipolar transistors.

An ion sensitive field effect transistor of the signal processing circuit may be coupled to a metal oxide semiconductor transistor in a current mirror arrangement. Preferably, the ion sensitive field effect transistor and the metal oxide semiconductor transistor are substantially electrically matched, with both being operated in the weak inversion mode.

In certain example embodiments, the ISFET comprises a membrane coating on the gate, the membrane having a sensitivity to hydrogen ion concentration in an electrolyte to which the membrane is exposed.

The signal processing circuit may comprises a multiplier-divider circuit arranged to receive the output of the current mirror and to invert the output signal of the current mirror, thereby providing an output signal which is directly proportional to hydrogen ion concentration.

According to a second aspect of the technology disclosed herein there is provided a method of monitoring a property of a medium using an ion sensitive field effect transistor, the method comprising:

biasing the ion sensitive field effect transistor in the weak inversion region;
exposing the ion sensitive field effect transistor to said medium; and
analysing an output of the ion sensitive field effect transistor which varies in dependence upon said property.

Preferably, said step of analysing an output current of the ion sensitive field effect transistor comprises deriving a current which is proportional to the value of the parameter being monitored.

According to a third aspect of the technology disclosed herein there is provided a digital signal processing circuit, one or more switches of the circuit being provided by an ion sensitive field effect transistor.

The or each ion sensitive field effect transistor comprises an analyte sensitive membrane which is exposed in use to a medium to be monitored.

The digital signal processing circuit may be a comparator for comparing a value of a parameter measured by the ion sensitive field effect transistor with a threshold value, the circuit comprising an ion sensitive field effect transistor and a metal oxide semiconductor transistor arranged in an inverter configuration. Preferably, one of the ion sensitive field effect transistor and the metal oxide semiconductor transistor is an n-channel device and the other is a p-channel device.

The digital signal processing circuit may be arranged to implement one or more of the following functions: AND, NAND, OR, XOR, NOR.

Preferably, the digital signal processing circuit uses CMOS logic. Alternatively, it may use NMOS or PMOS logic.

Preferably, the digital signal processing circuit comprises biasing means for biasing the or each ion sensitive field effect transistor in the weak inversion region.

According to a fourth aspect of the technology disclosed herein there is provided a method of implementing a logical function having as one of its inputs the value of a parameter of a medium, the method comprising:

configuring an ion sensitive field effect transistor to operate as a switch of a logic circuit;
exposing the ion sensitive field effect transistor to said medium.

DETAILED DESCRIPTION

Figure 3:
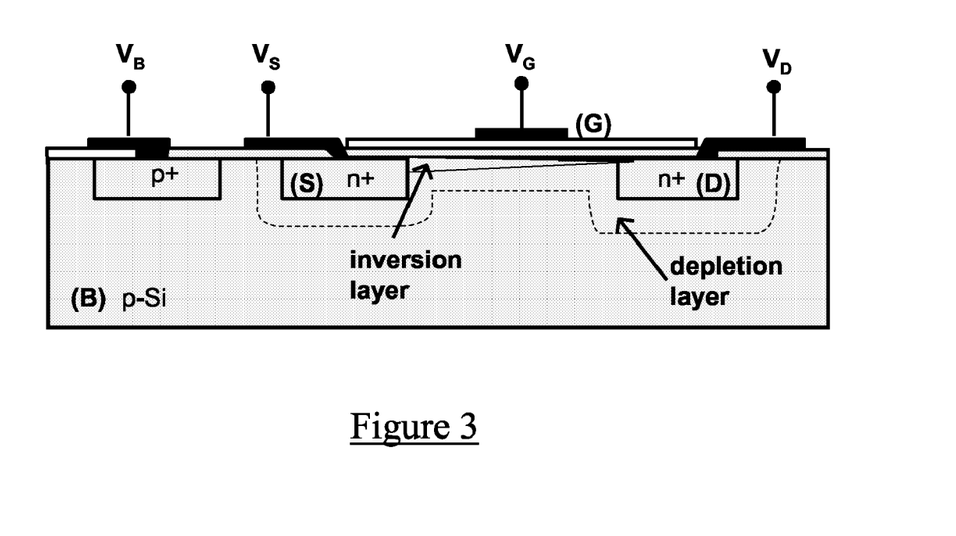
FIG. 3 illustrates schematically a p-channel silicon MOSFET.

An n-channel FET such as that illustrated in FIG. 3 is a four terminal device, consisting of a p-type silicon substrate (B) and two highly-doped n-type wells known as the source (S) and the drain (D). The silicon surface is covered with a silicon dioxide insulator. A polysilicon gate contact (G) controls the charge within the region under the insulator surface between source and drain, known as the channel.

As the voltage $V_G$ applied to the gate is increased, positive charge is initially repelled from the channel forming a depletion layer with no mobile charge carriers and a net negative charge. As the gate voltage is further increased, this depletion layer widens until electrons begin to be drawn from source and drain into the channel, forming an inversion layer. The transistor is usually operated above a certain threshold voltage for which the channel is strongly inverted and the mobile electrons in the inversion layer drift across the channel when a potential difference is applied between drain and source. As already noted, for this mode of operation drain current is related to the gate voltage by a square law or linear relation.

The so-called "weak inversion" mode of operation involves maintaining the gate voltage lower than the threshold voltage such that the channel is depleted and only a thin inversion layer exists. In weak inversion, the mobile charge in the thin inversion layer is too low to contribute significantly to any drift current across the horizontal electric field. Drain current in weak inversion is due to the diffusion of electrons across a concentration gradient between source and drain. Since the electron concentrations at source and drain and along the channel are related to the barrier potentials at those points by the Boltzmann distribution, it follows that the drain current is exponentially related to Vs, Vd and Vg relative to Vb, scaled by the thermal voltage $U_T$=kT/q or RT/F. That is:

$$I_d = I_0 \exp(V_G/nU_T)[\exp(-V_S/U_T) - \exp(-V_D/U_T)] \quad (2)$$

where $I_0$ is the pre-exponential multiplier and n is the sub-threshold slope factor.

For the ISFET, the reference electrode acts as a remote gate and the chemically sensitive membrane deposited on top of the $SiO_2$ insulator is exposed directly to the sample solution. The extent of inversion in the channel beneath the insulator is dependent not only on the voltage applied to the reference electrode, but also on the accumulation of charge from ions in solution on the sensing membrane. The build-up of ions at the surface of the membrane is related to the concentration of the ionic species in the sample by the site binding and Gouy-Chapman double layer models. Since any positive charge build-up on the membrane surface must be mirrored by a negative charge build-up in the channel, changes in ionic concentration of the sample will be reflected directly in the ISFET's weak inversion drain current.

A knowledge of the relationship between membrane surface charge and species concentration, together with the fact that weak inversion ISFET current is proportional to membrane surface charge, means that electronic circuits performing simple mathematical manipulation can be used to obtain a direct relation between species concentration and current even in ChemFETs and EnFETs. Furthermore, the sensitivity of the weak inversion ISFET current to ion concentration is independent of temperature, since the temperature-scaled Boltzmann distributions of both the electrons in the channel and the ions in solution cancel each other out.

The large-signal equation for drain current in a MOSFET biased in the weak inversion region is given by:

$$I_D = I_o \exp\left(\frac{V_{GS}}{nU_T}\right)\left(1 - \exp\left(\frac{-V_{DS}}{U_T}\right)\right) \quad (3)$$

$$= \left[2n\frac{KW}{L}U_T^2 \exp\left(\frac{V_{GS} - V_{T0}}{nU_T}\right)\exp\left(\frac{(n-1)V_{BS}}{nU_T}\right)\right]$$

$$\left(1 - \exp\left(\frac{-V_{DS}}{U_T}\right)\right)$$

where $\beta = KW/L$, $V_{TO}$ is the threshold voltage for $V_{BS}=0$ and n is the sub-threshold slope factor and saturation is assumed for $V_{DS} > 4U_T$. This equation also holds for a weakly-inverted ISFET, since all additional chemical phenomena are represented as the modulation of its threshold voltage by a potential across the electrolyte which is linearly proportional to pH. Since pH is exponentially related to hydrogen ion concentration, a direct relation between hydrogen ion concentration and weak inversion drain current can be developed.

Any circuit which extracts the potential across the electrolyte and converts it to a weak inversion current signal is of significant interest for real-time chemical signal processing since hydrogen ion concentration is a more natural parameter for signal processing than pH. The current mirror, illustrated in FIG. 4, is the simplest of such circuits.

Figure 4:
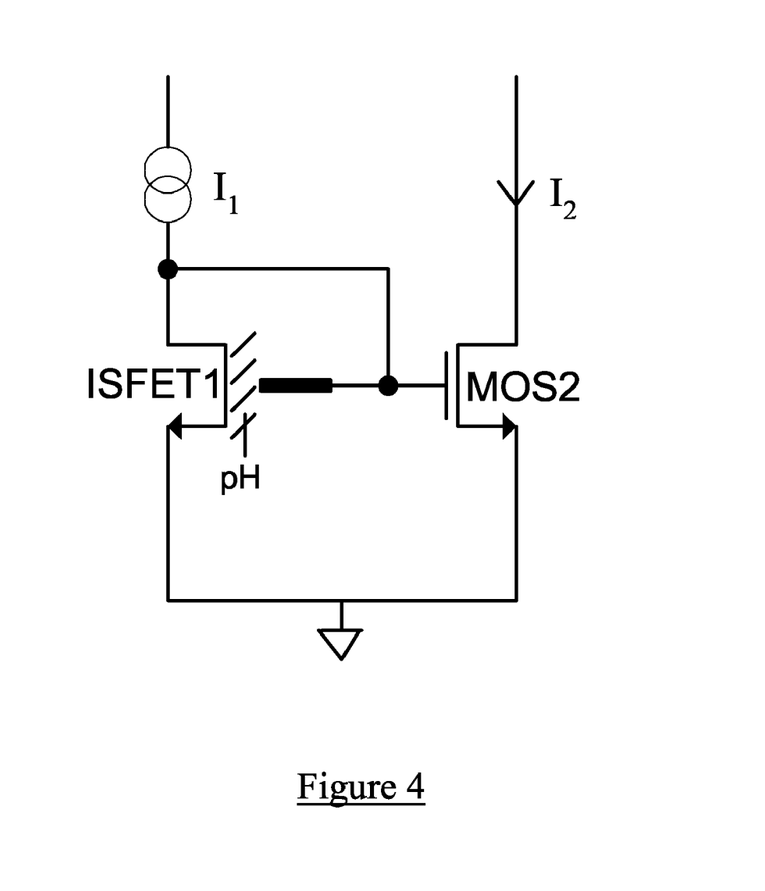
FIG. 4 illustrates a current mirror comprising an ISFET.

If a diode-connected ISFET is biased with a current source and its reference electrode connected to the gate of a MOSFET as in FIG. 4, and assuming geometrically and electrically-matched devices and ignoring $\Delta V_{DS}$ error, then $I_1 \neq I_2$ because of the $\Delta V_{th}$ between the ISFET and the MOSFET, which is known from (1) to be equal to $V_{chem}$.

Using equation (3) for perfectly matched, saturated devices:

$$\frac{I_{D2}}{I_{D1}} = \exp\left(\frac{V_{chem}}{nU_T}\right) \quad (4)$$

Substituting in the logarithmic relation between pH and hydrogen ion concentration, $pH = -\log_{10}[H^+]$, we find that the current ratio $I_{D2}/I_{D1}$ is proportional to a known power of hydrogen ion concentration and is independent of temperature effects:

$$\frac{I_{D2}}{I_{D1}} = \exp\left(\frac{\gamma}{nU_T}\right)\exp\left(\frac{2.3U_T \alpha pH}{nU_T}\right) \quad (5)$$

-continued $$= \exp\left(\frac{\gamma}{nU_T}\right)\exp\left(\frac{-\alpha \ln[H^+]}{n}\right)$$

$$= K_{chem} \cdot [H^+]^{-\alpha/n}$$

This significant result shows that the drain current in a weakly-inverted ISFET is controlled exponentially by its gate-source and bulk-source potentials, and is scaled by a temperature-independent parameter which is proportional to a known power (less than unity since $0<\alpha<1$ and $n>1$) of the hydrogen ion concentration, that is:

$$I_{D(ISFET)} = I_{D(MOS)} K_{chem}^{-1} \cdot [H^+]^{+/n} \quad (6)$$

The temperature insensitivity of the ISFET biased in the weak inversion region makes it ideal for use in the transduction stage of a chemical sensor. Use of MOSFETs in weak inversion is also advantageous for on-chip processing circuitry since the exponential relation between drain current and terminal voltages can be exploited to implement mathematical manipulation using very simple, low-power circuits.

In order to obtain an output current which is directly proportional to [H$^+$], some further manipulation of equation (5) is required. Translinear circuits which exploit the linear relation between transconductance and drain current in sub-threshold MOS transistors can be used to perform multiplication, division and power law functions on current signals (although bipolar transistors exhibiting this relationship might alternatively or additionally be used).

Figure 5:
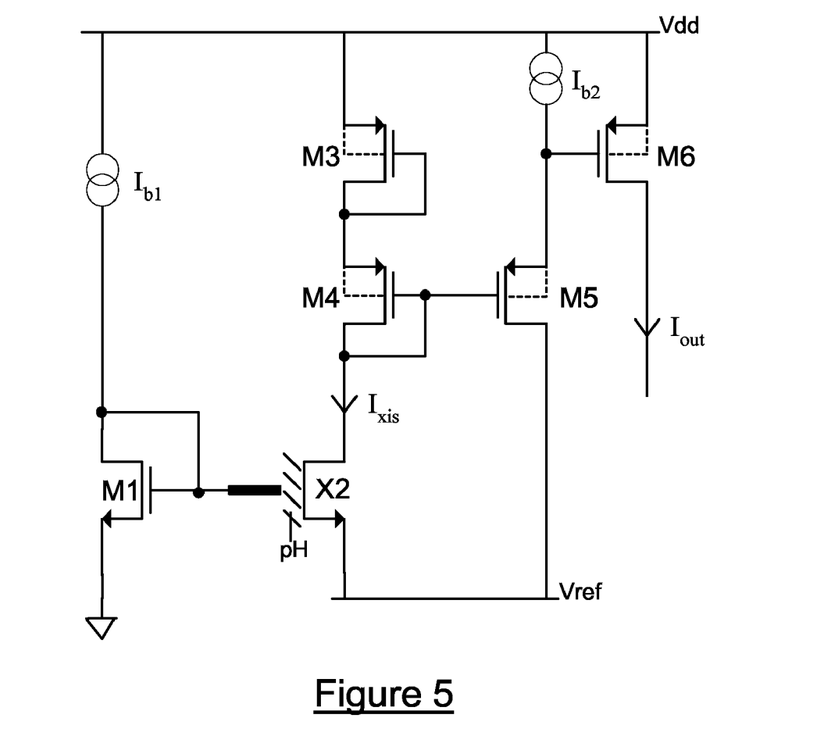
FIG. 5 illustrates an HCell for measuring hydrogen ion concentration.

The circuit illustrated in FIG. 5 is presented as an example of an input stage whose output is a current $I_{out}$ directly proportional to the number of H$^+$ ions (protons) in the bulk of the electrolyte. This circuit is referred to here as an "HCell". It is illustrative of how apt it is to exploit the exponential behaviour of field effect transistors in weak inversion to obtain real chemical parameters directly. The ISFET used in the HCell has its ion-sensitive membrane chemically tailored such that its pH-sensitivity gives $\alpha/n = 0.5$.

Assuming saturation and ignoring $\Delta V_{DS}$ error, it can be shown from equation (3) that the drain currents between the ISFET X2 and MOSFET M1 are related by:

$$\frac{I_{xis}}{I_{b1}} = \frac{n_2 \beta_2}{n_1 \beta_1} \exp\left(\frac{-\Delta V_{T0}}{nU_T}\right) \exp\left(\frac{(n-1)(V_{b2} - V_{b1})}{nU_T}\right) \exp\left(\frac{V_{S1} - V_{S2}}{U_T}\right) \quad (7)$$

where $$\Delta V_{T0} = V_{T0(ISFET)} - V_{T0(MOS)} = V_{chem}$$

For the circuit shown in FIG. 5, assuming geometrically and electrically matched devices with equal device dimensions and bulks connected to ground, equation (7) becomes:

$$\frac{I_{xis}}{I_{b1}} = \exp\left(\frac{-\gamma - 2.3\alpha U_T pH}{nU_T}\right)\exp\left(\frac{-V_{ref}}{U_T}\right) \quad (8)$$

$$= K_{chem}[H^+]^{0.5}\exp\left(\frac{-V_{ref}}{U_T}\right)$$

where $$K_{chem} = \exp\left(\frac{-\gamma}{nU_T}\right)$$

The reference voltage $V_{ref}$ is used to set the bias point such that both M1 and X2 operate in weak inversion. The limit on pH input range is the voltage range of the operable weak inversion region and the pH sensitivity S. For weak inversion regions of approximately 400 mV $V_{GS}$ range, typical ISFETs with sensitivities of 50 mV/pH have 7 or 8 pH units of dynamic range.

Transistors M3 to M6 form a translinear loop for which, using the translinear principle, we obtain the relation:

$$I_{out} = \frac{I_{xis}^2}{I_{b2}}$$

Substituting in the result from (8)

$$I_{out} = \frac{I_{b1}^2 \exp\left(\frac{-2V_{ref}}{nU_T}\right) K_{chem}^2 [H+]}{I_{b2}} \quad (9)$$

Setting Ib1=Ib2 we get a direct relation between the current ratio Iout/Ib1 and [H+]:

$$\frac{I_{out}}{I_{b1}} = \exp\left(\frac{-2V_{ref}}{nU_T}\right) K_{chem}^2 [H+] \quad (10)$$

This ratiometric approach to signal processing reduces the temperature dependence of the circuit assuming that the devices are in close proximity. Using a Proportional To Absolute Temperature (PTAT) reference voltage $V_{ref}$ and assuming that $K_{chem}$ and α are temperature-independent to a first order approximation, we see that the current ratio is directly proportional to hydrogen ion concentration with inherent temperature compensation.

The circuit of FIG. 5 was simulated on AMS 0.8μ technology using a simplified version of the Martinoia macromodel for a silicon nitride ISFET with $pH_{pzc}$=3 and perfectly linear pH sensitivity (constant α for all pH and temperature). It was found that n≈1.43 and α was chosen to be 0.715 corresponding to a sensitivity of 42.6 mV/pH at T=300K.

Figure 6:
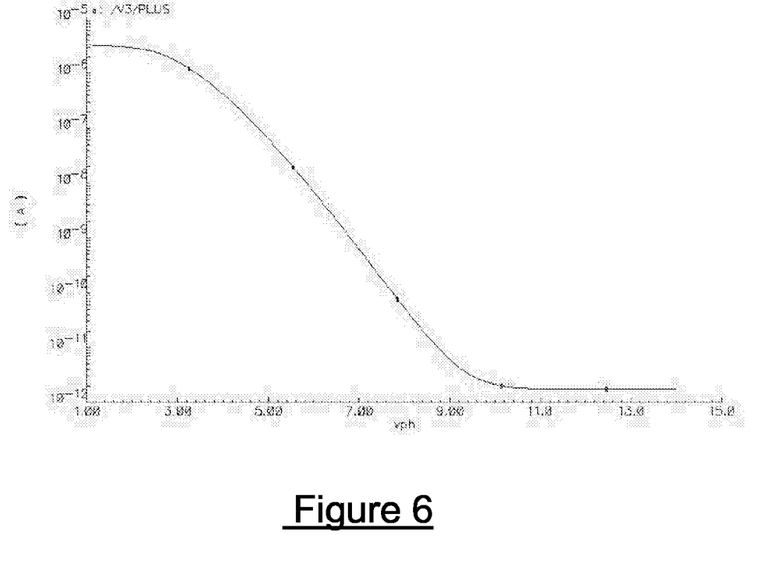
FIG. 6 shows the IV characteristic of the Hcell of FIG. 5.

Vdd=1.8V, Ib1=Ib2=10 nA, and Vref was chosen to be 50 mV in order to centre the region of operation on pH 7. The output current, shown in FIG. 6 gives good linearity for the pH range 5 to 9, for which $$\frac{d\ln(Iout)}{d\text{pH}} = -2.303 \pm 0.19.$$

Large dimensions (W=432 μm, L=8 μm) were chosen for X2 and M1 to minimise the effect of matching errors. W/L for transistors M3 to M6 was 40 μm/8 μm.

Extending the principles presented herein to a circuit with several ISFETs each coding a different ionic concentration, would allow any chemical equation involving products, quotients and power law relations of ionic concentration to be processed in real time. Exploiting all four terminals of the ISFET by use of the bulk or 'back gate' as a second input for translinear manipulations further increases the flexibility of these principles. Furthermore, the inclusion of capacitors opens up this principle to a whole field of reaction kinetics differential equations.

The ISFET-MOSFET mirror is the simplest current mode input stage and has been presented here to illustrate how apt it is to convert the threshold voltage modulation caused by chemical phenomena to a current. Replacing the MOSFET in this configuration with an almost pH-insensitive ISFET (known as a REFET) would permit the use of a solid-state quasi-reference electrode since the unstable and unknown electrode potential is common to both ISFET and REFET and is cancelled in the current mirror topology. The difference in threshold voltage $\Delta V_{TH}$ is smaller between an ISFET and a REFET than between an ISFET and a MOSFET, decreasing $\Delta V_{DS}$ errors and reducing the required $V_{bias}$, thereby reducing power consumption. Matching could also be improved. For a more robust circuit with higher SNR, a fully differential input stage should be used.

Smart sensing concepts based on weak inversion operation of the transistor applications beyond chemical discrimination using the selectivity of the membranes include:

Real-time reaction monitoring and analytical data processing

DNA-sequencing

Fast acid-base titrations using kinetic models to extract the analytical information sought, well before reaching the equivalence point Implementation of "chemical decision trees" using ISFETs and other sensors directly as logic (true/false) devices with adjustable thresholds Medical diagnostics using real-time monitoring of blood and urine metabolite ratios Neural bridges Impurity detection In addition to its suitability for use in a transducer input stage, the ISFET operating in the weak inversion can provide a basic building block for the digital processing of chemically related signals.

Figure 7:
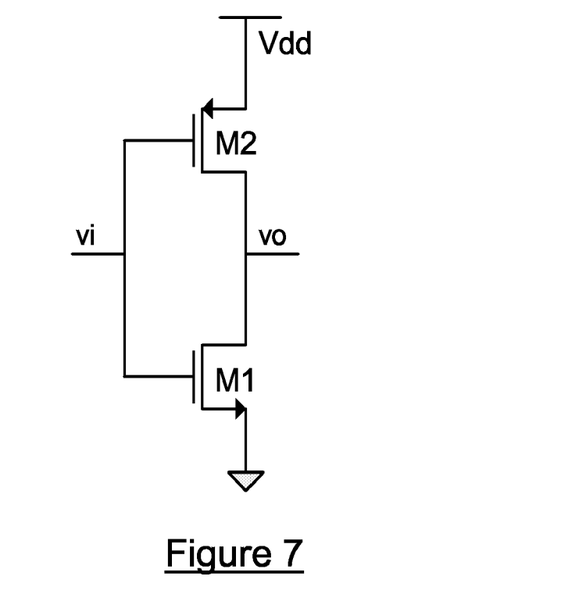
FIG. 7 illustrates schematically a CMOS inverter.
Figure 8:
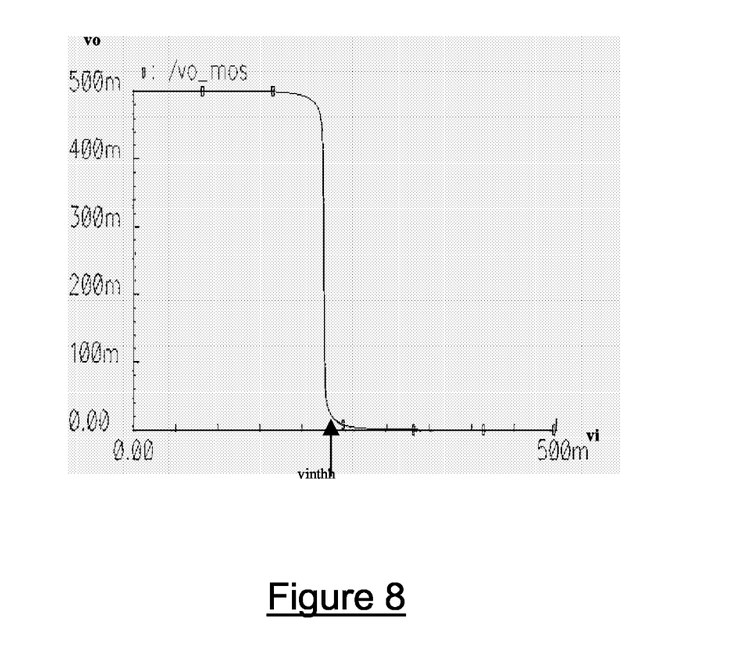
FIG. 8 shows the switching characteristic of the inverter of FIG. 7.

The standard CMOS inverter illustrated in FIG. 7 has the voltage transfer characteristic shown in FIG. 8, when operated in the weak inversion region. For the weak inversion region, in saturation and assuming $V_{BS}$=0, the drain current is given by:

$$I_D = 2n\beta U_T^2 \exp\left(\frac{V_{GS} - V_{T0}}{nU_T}\right) \quad (11)$$

where n is the sub-threshold slope parameter, β=KW/L, $U_T$ is the thermal voltage and $V_{T0}$ is the intrinsic threshold voltage.

At the switching threshold Vinth, M1 and M2 have equal drain currents.

$$V_{inth} = \frac{V_{DD} - |V_{T0p}| + \ln\left(\frac{I_{sn}}{I_{sp}}\right) V_{T0n}}{1 + \ln\left(\frac{I_{sn}}{I_{sp}}\right)} \quad (12)$$

where sub-threshold slopes for NMOS and PMOS are assumed equal.

Figure 9:
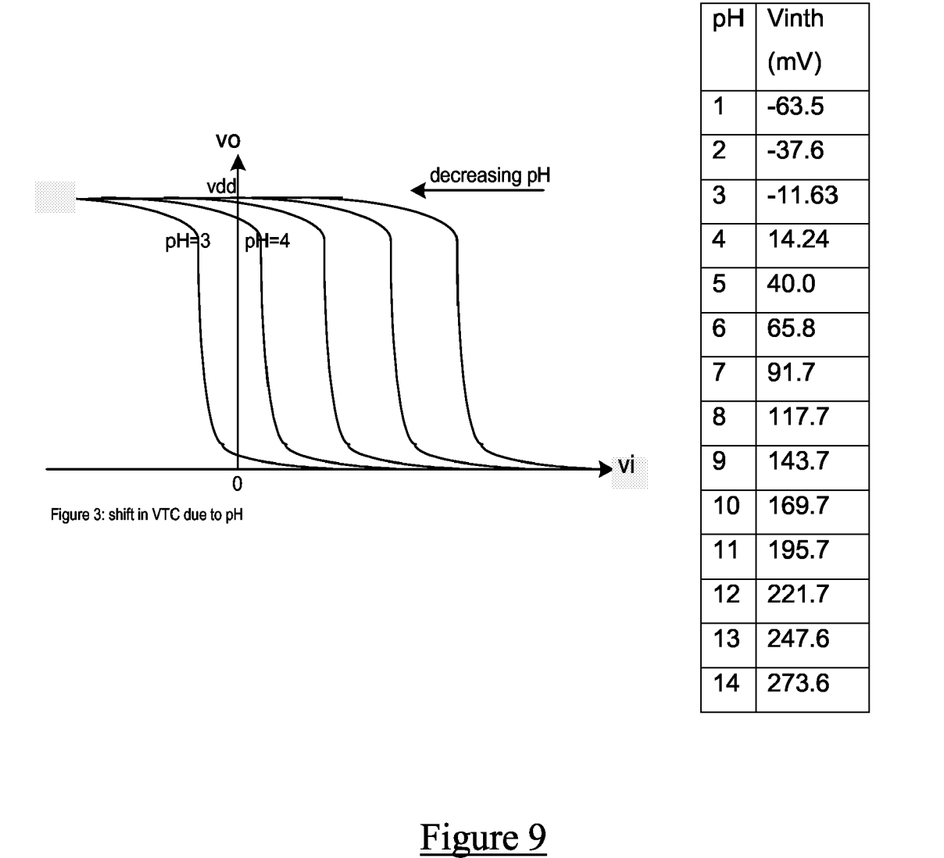
FIG. 9 illustrates the shift in switching threshold caused by changing pH in a CMOS inverter comprising an ISFET.
Figure 10:
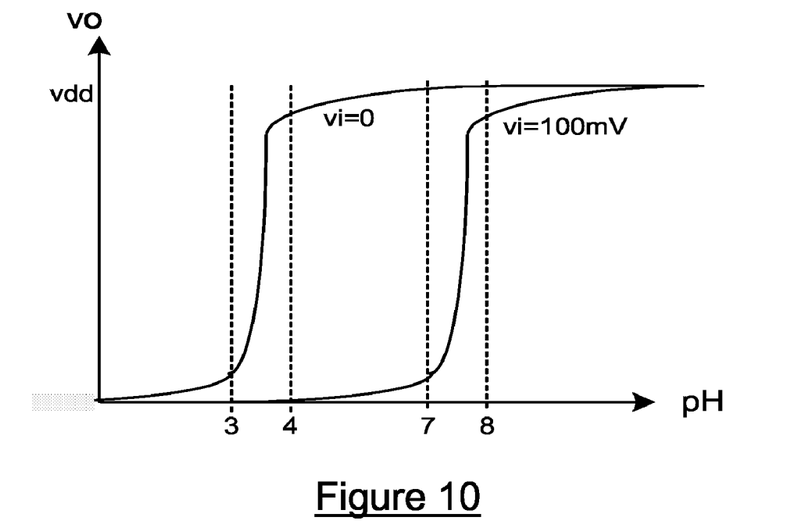
FIG. 10 shows the switching properties of an ISFET inverter at differing input voltages.

If the NMOS M1 of FIG. 7 is replaced by an n-channel ISFET, then, given that $V_{th(ISFET)} = V_{th(MOS)} + V_{chem}$, the switching threshold will be given as:

$$V_{inth} = \frac{V_{DD} - |V_{TOp}| + \ln\left(\frac{I_{sn}}{I_{sp}}\right)[V_{TOn} + V_{chem}]}{1 + \ln\left(\frac{I_{sn}}{I_{sp}}\right)} \quad (13)$$

i.e. a decrease in switching threshold for pH<11 and an increase for pH>11. FIG. 9 illustrates the shift in switching threshold caused by changing pH. A consequence of this characteristic is that if vi is fixed, then switching will occur exclusively due to changes in pH. Moreover, the pH threshold at which this switching occurs can be set by the choice of vi as shown in FIG. 10. For illustration, it is shown that the output is high for pH≧4 when vi is fixed at 0V and for pH≧8 when vi=100 mV.

The significance of this is that the circuit of FIG. 7 can be used as a comparator whose output is high for a pH greater than a threshold defined by the fixed input voltage on the gate, vi.

Figure 11:
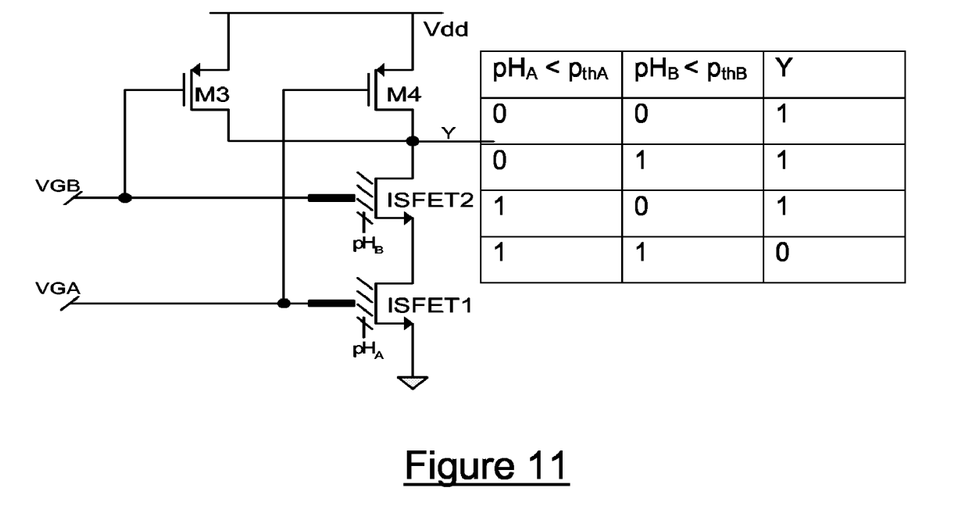
FIG. 11 shows an ISFET based NAND gate and the corresponding truth table.
Figure 12:
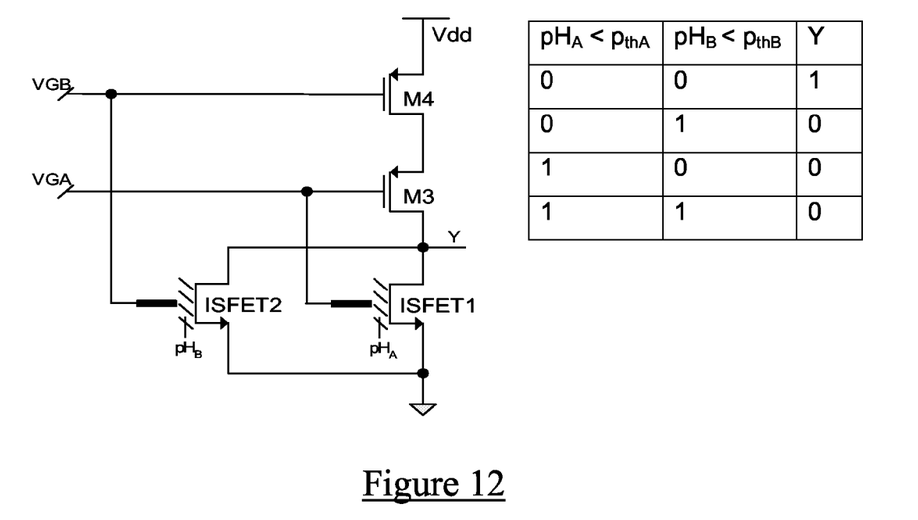
FIG. 12 shows an ISFET based NOR gate and the corresponding truth table.

Logic gates may also be constructed using the ISFET operating in the weak inversion region. In the circuit of FIG. 11 for example, $v_{GA}$ sets the pH threshold $p_{thA}$ and $v_{GB}$ sets $p_{thB}$. The n-channel ISFET is in saturation for pH<$p_{th}$. The output Y will only be 0 when both ISFETs are in saturation; for all other states the output is 1 as shown in the NAND truth table. Viewed from another perspective, we can say that the output is high for $pH_A \geq p_{thA}$ OR $pH_B \geq p_{thB}$ By a similar analysis, the output in the circuit of FIG. 12 is high only when $pH_A \geq p_{thA}$ AND $pH_B \geq p_{thB}$ as can be deduced from the NOR truth table (assuming again that VGA sets the pH threshold $p_{thA}$ and $v_{GB}$ sets $p_{thB}$).

It has been shown that ISFETs can be used to implement the basic logic gates, triggered not by 0 and 1 on the gate input, but by a pH < or > than a chosen threshold. ISFETs are therefore well-suited to the direct implementation of more complex logic functions.

Whilst the preferred operating mode for ISFETs/MOSFETs forming such digital circuits is the weak inversion mode, this is not essential, and they might alternatively be operated in the saturation mode. Circuits may use a combination of weak inversion mode and saturation mode devices.

It will be appreciated by those of skill in the art that various modifications may be made to the above described embodiments without departing from the scope of the invention. In one modification, the single gate ISFET described above is replaced with a multi-gate ISFET. In another modification, the "back-gate" or substrate is used as an additional input of the device.

It will also be appreciated that "dynamical" mathematical systems including instantaneous companding systems can be created by adding capacitors to the gates of ISFETs (and other MOSFETs of the associated circuitry), thus converting the characteristics into large signal non-liner time domain biochemical functions, eg log domain filters and processors. Such functionality relies upon the exponential/logarithmic characteristics of the weak inversion MOSFET.

The invention claimed is:

1. A signal processing circuit comprising an ion sensitive field effect transistor, a reference electrode for the ion sensitive field effect transistor, a metal oxide semiconductor transistor having its gate coupled to the reference electrode, and a biasing circuit biasing the ion sensitive field effect transistor and the metal oxide semiconductor field effect transistor to operate in a weak inversion region and to provide an output current signal.

2. A circuit according to claim 1, wherein the ion sensitive field effect transistor, metal oxide semiconductor field effect transistor, and the biasing circuit are integrated onto a single chip.

3. A circuit according to claim 1, wherein the signal processing circuit is configured to determine, in use, the hydrogen ion concentration of a medium to which the ion sensitive field effect transistor is exposed.

4. A circuit according to claim 1, wherein said ion sensitive field effect transistor is coupled to said metal oxide semiconductor transistor in a current mirror arrangement.

5. A circuit according to claim 4, wherein ion sensitive field effect transistor and the metal oxide semiconductor transistor are substantially electrically matched.

6. A circuit according to claim 1, wherein the signal processing circuit comprises a multiplier-divider circuit arranged to receive the output of the current mirror and to invert the output signal of the current mirror, thereby providing an output signal which is directly proportional to hydrogen ion concentration, the multiplier-divider circuit comprising a plurality of metal oxide semiconductor field effect transistors and a biasing circuit biasing these metal oxide semiconductor field effect transistors to operate in the weak inversion region.

7. A circuit according to claim 1, wherein the ion sensitive field effect transistor comprises a membrane coating on the gate, the membrane having a sensitivity to hydrogen ion concentration in an electrolyte to which the membrane is exposed.

8. A method of monitoring a property of a medium using an ion sensitive field effect transistor, the method comprising:
coupling a gate of a metal oxide semiconductor field effect transistor to a reference electrode for the ion sensitive field effect transistor;
biasing the ion sensitive field effect transistor and the metal oxide semiconductor field effect transistor in a weak inversion region;
exposing the ion sensitive field effect transistor to said medium; and
analysing an output current of the ion sensitive field effect transistor which varies in dependence upon said property.

\* \* \* \* \*